United States Patent
Richards

(10) Patent No.: US 6,846,491 B1
(45) Date of Patent: Jan. 25, 2005

(54) CLEAR, POLYMERIC GEL COMPOSITION AND METHOD FOR PRODUCING THE SAME

(75) Inventor: Randall Richards, Canton, GA (US)

(73) Assignee: International Fragrance & Techology, Canton, GA (US)

( * ) Notice: Subject to any disclaimer, the term of this patent is extended or adjusted under 35 U.S.C. 154(b) by 114 days.

(21) Appl. No.: 10/040,412

(22) Filed: Jan. 7, 2002

Related U.S. Application Data

(60) Provisional application No. 60/315,402, filed on Aug. 28, 2001.

(51) Int. Cl.$^7$ ............................................. A01N 25/04
(52) U.S. Cl. ..................... 424/405; 424/400; 424/401; 424/484
(58) Field of Search ................................. 424/484, 400, 424/401, 76.3, 76.4, 78.06, 78.17

(56) References Cited

U.S. PATENT DOCUMENTS

| | | | |
|---|---|---|---|
| 3,821,363 A | * | 6/1974 | Black et al. .................. 424/59 |
| 4,362,841 A | | 12/1982 | Minatono et al. |
| 4,497,663 A | | 2/1985 | Fisher et al. |
| 4,857,563 A | | 8/1989 | Croft et al. |
| 5,334,691 A | | 8/1994 | Gould et al. |
| 5,354,550 A | * | 10/1994 | Collins et al. ................. 424/49 |
| 5,633,341 A | | 5/1997 | Abend |
| 5,780,527 A | | 7/1998 | O'Leary |
| 5,792,816 A | | 8/1998 | Abend |
| 5,844,047 A | | 12/1998 | Abend |

FOREIGN PATENT DOCUMENTS

| | | |
|---|---|---|
| FR | 2455068 | 11/1980 |
| WO | 0178792 | 10/2001 |

* cited by examiner

*Primary Examiner*—Neil S. Levy
(74) *Attorney, Agent, or Firm*—Sonnenschein Nath & Rosenthal LLP; Brian R. McGinley

(57) ABSTRACT

Disclosed is a clear, crosslinked, polymeric gel composition that is the reaction product of a microemulsion containing (a) from 1–70 wt. %, preferably from 1–40 wt. %, and more preferably from 10–25 wt. % of an anhydride functionalized polymer, (b) from 0.1–40 wt. %, preferably from 0.1–20 wt. %, and most preferably from 0.5–5 wt. % of a cross-linking agent, (c) from 0.01–50 wt. %, preferably from 0.1–20 wt. %, and more preferably from 0.5–10 wt. % surfactant, (d) from 0.01–30 wt. %, preferably from 0.1–10 wt. %, and more preferably from 0.1–5 wt. % water, and (e) from 10.0–95.0 wt. % of a hydrophobic liquid, based on the total weight of the polymeric gel composition. The gel composition is prepared by combining the anhydride functionalized polymer, the cross-linking agent, the surfactant, the water, and the hydrophobic liquid-form a microemulsion and then gelling the microemulsion.

12 Claims, No Drawings

CLEAR, POLYMERIC GEL COMPOSITION AND METHOD FOR PRODUCING THE SAME

RELATED APPLICATION

Pursuant to 37 C.F.R § 1.78(a)(3) this application claims the benefit of U.S. provisional application Ser. No. 60/315,402 filed Aug. 28, 2001.

BACKGROUND OF THE INVENTION

1. Field of the Invention

This invention relates to the chemical arts. In particular, it relates to a polymeric gel composition and a method for producing the same.

2. Discussion of the Related Art

Clear, hydrophobic polymeric gel compositions have been described in U.S. Pat. Nos. 4,497,663, 4,857,563, 5,780,527, and in WO 01/78792. It is a drawback of such hydrophobic gels, that the inclusion of water, even at extremely low levels, results in gels that are cloudy or opaque. It is a further drawback, that if water is included in these gels, the gels typically exhibit a "wetness" or syneresis, because of the incompatibility of the hydrophobic material and the water. It is a still further drawback that the hydrophobic gels are incompatible with many water soluble additives including pH color indicators, fluorescent, dyes, water soluble dyes, water soluble fragrance components, and water soluble cross-linking agents.

Hydrophilic polymer compositions have been described in U.S. Pat. Nos. 5,334,691 and 4,362,841. The gels have been shown to contain between 0.1–70 wt. % water. It is a drawback of these gels that when hydrophobic liquids, such as perfumes, insecticides, and insect repellants, are added, the gels are not clear, but are opaque, translucent, or heterogeneous.

Until now no system has been described that produces a gel composition, compatible with both hydrophobic liquids and water soluble materials, in a clear gel that is aesthetically pleasing and functionally appropriate.

SUMMARY OF THE INVENTION

Now in accordance with the invention there has been found a novel, clear, crosslinked, polymeric gel composition and a novel method for producing the gel composition. The gel composition is the reaction product of a microemulsion containing (a) from 1–70 wt. %, preferably from 140 wt. %, and more preferably from 10–25 wt. % of an anhydride functionalized polymer, (b) from 0.1–40 wt. %, preferably from 0.1–20 wt. %, and most preferably from 0.5–5 wt. % of a cross-linking agent, (c) from 0.01–50 wt. %, preferably from 0.1–20 wt. %, and more preferably from 0.5–10 wt. % surfactant, (d) from 0.01–30 wt. %, preferably from 0.1–10 wt. %, and more preferably from 0.1–5 wt. % water, and (e) from 10.0–95.0 wt. % of a hydrophobic liquid, based on the total weight of the polymeric gel composition. In preferred embodiments, the combined proportion of (d) and (e) equals at least 30 wt. %, based on the total weight of the polymeric gel composition.

Representative anhydride functionalized polymers include maleinized polybutadiene polymers, maleinized polyisoprene polymers, maleinized polybutadiene/styrene polymers or mixtures thereof. Representative cross-linking agents include polyamine cross-linking agents. Representative surfactants include anionic and nonionic surfactants. Representative hydrophobic liquids include perfumes, insecticides, and insect repellants. In a preferred embodiment where the hydrophobic liquid is an insect repellant, the insect repellant is N,N-Diethyl-m-toluamide.

In some embodiments, the microemulsion additionally contains a water soluble additive. Useful water soluble additives include water soluble colorants, water soluble dyes, water soluble pH color indicators, water soluble pigments, water soluble fragrances, and water soluble flavor materials.

The gel composition is formed from a microemulsion that contains (a) from 1–70 wt. %, preferably from 1–40 wt. %, and more preferably from 10–25 wt. % of an anhydride functionalized polymer, (b) from 0.1–40 wt. %, preferably from 0.1–20 wt. %, and most preferably from 0.5–5 wt. % of a cross-linking agent, (c) from 0.01–50 wt. %, preferably from 0.1–20 wt. %, and more preferably from 0.5–10 wt. % surfactant, (d) from 0.01–30 wt. %, preferably from 0.1–10 wt. %, and more preferably from 0.1–5 wt. % water, and (e) from 10.0–95.0 wt. % of a hydrophobic liquid, based on the total weight of the polymeric gel composition. The microemulsion is then gelled to form the clear, crosslinked, polymeric gel composition.

In some embodiments, the microemulsion is gelled in a mold and the resulting gel composition is then removed from the mold. And in some embodiments, the microemulsion is formed by combining a first premix containing the cross-linking agent and one or more of at least a portion of the hydrophobic liquid, the surfactant, and the water with a second premix containing the anhydride functionalized polymer and one or more of at least a portion of the hydrophobic liquid, the surfactant, and the water. In some preferred embodiments, the first premix contains the cross-linking agent, the surfactant, the water, and a first portion of the hydrophobic liquid. And in some preferred embodiments, the second premix contains the anhydride functionalized composition, and a second portion of the hydrophobic liquid.

DETAILED DESCRIPTION OF THE PREFERRED EMBODIMENTS

The present invention provides a clear, crosslinked, polymeric gel made from a microemulsion that contains (a) from 1–70 wt. %, preferably from 1–40 wt. %, and more preferably from 10–25 wt. % of an anhydride functionalized polymer, (b) from 0.1–40 wt. %, preferably from 0.1–20 wt. %, and most preferably from 0.5–5 wt. % of a cross-linking agent, (c) from 0.01–50 wt. %, preferably from 0.1–20 wt. %, and more preferably from 0.5–10 wt. % surfactant, (d) from 0.01–30 wt. %, preferably from 0.1–10 wt. %, and more preferably from 0.1–5 wt. % water, and (e) from 10.0–95.0 wt. % of a hydrophobic liquid, based on the total weight of the polymeric gel composition. In preferred embodiments, the combined proportion of (d) and (e) equals at least 30 wt. %, based on the total weight of the polymeric gel composition.

The microemulsion contains from 1–70 wt. %, preferably from 1–40 wt. %, and more preferably from 10–25 wt. % of an anhydride functionalized polymer. Useful anhydride functionalized polymers are polymers made by reacting maleic anhydride with a suitable polymer, such as butadiene, isoprene, chloroisoprene, butadiene-styrene, other polyunsaturated hydrocarbons, including mixtures thereof, resulting in a covalent attachment of maleic anhydride to the polymer.

Examples of suitable anhydride functionalized polymers include maleinized polybutadiene (such as Ricon 131MA10, available from Sartomer Co., Exton, Pa., and Lithene N4-9000-MA10, available from Synthomer Ltd., Essex, U.K.), maleinized polyisoprene (such as LIR-403, available from Kurary Co., Ltd., Tokyo, Japan), maleinized polybutadiene-styrene (such as Ricon 184), maleinized polychloroisoprene, maleinized polybutadiene-isoprene, and maleinized vegetable oil. Maleinized polybutadiene and maleinized polyisoprene are preferred. Maleinized polybutadiene is most preferred.

The microemulsion also contains from 0.1–40 wt. %, preferably from 0.1–20 wt. %, and most preferably from 0.5–5 wt. % of a cross-linking agent for the anhydride functionalized polymer. It is an advantage of the invention that the cross-linking agent can be a water soluble cross-linking agent. Representative water soluble cross-linking agents include polyoxyethylene diamine, such as Jeffamine D 2003.

Suitable cross-linking agents are materials that react with an anhydride functionalized polymer to form a cross-linked polymer. Typically, the anhydride functionalized polymer and the cross-linking agent are included in a molar ratio of between about 3:1 and 0.5:1, preferably of about 1:1, based on the molar ratio of the functional groups which are present.

Representative cross-linking agents include, but are not limited to, compounds that contain an amine, alcohol, or thio functional group. Suitable cross-linking agents can also contain a combination of one or more thio, amine and alcohol functional groups. Also useful are the solid, heat-activated cross-linking agents disclosed in U.S. Pat. No. 5,844,047 (which patent is herein incorporated by reference).

Preferred cross-linking agents include polythios, polyols, and polyamines, with polyamines being the most preferred cross-linking agent. Suitable polyamine cross-linking agents include (1) diamines, including polyoxypropylenediamine (such as Jeffamine D-400, available from Huntsman Corp., Salt Lake City, Utah) and triethyleneglycoldiamine (such as Jeffamine XTJ-504) and (2) triamines, including polyoxypropylenetriamine (such as Jeffamine T-403 and XTJ-509). Also useful are hindered polyamines, such as the hindered polyamines described in U.S. Pat. No. 5,633,341 (which patent is herein incorporated by reference) and polyamines contained within molecular sieves, such as the polyamines described in U.S. Pat. No. 5,792,816 (which patent is herein incorporated by reference).

The microemulsion contains from 0.01–50 wt. %, preferably from 0.1–20 wt. %, and more preferably from 0.5–10 wt. % surfactant. Suitable surfactants include nonionic surfactants, amphoteric surfactants, zwitterionic surfactants, cationic surfactants, anionic surfactants and combinations thereof. Preferred surfactants are nonionic and anionic surfactants. Examples of nonionic surfactants are ethoxylated nonylphenol containing 4 moles of ethylene oxide (such as Surfonic N40, available from Huntsman Corp., Salt Lake City, Utah) and ethoxylated alcohols containing 3 moles of ethylene oxide (such as Surfonic L243 and Tergitol 15-S-3, available from Dow Chemical Co., Midland, Mich.). Examples of anionic surfactants are ethoxylated alkyl sulfates (such as Steol CS460, available from Stephan Company, Northfield, Ill.).

The microemulsion contains from 0.01–30 wt. %, preferably from 0.1–10 wt. %, and more preferably from 0.1–5 wt. % water and 10.0–95.0 wt. % hydrophobic liquid. In a preferred embodiment, the combined proportion of water and hydrophobic liquid equals at least 30 wt. %, based on the total weight of the polymeric gel composition.

Suitable hydrophobic liquids that can be used in accordance with the invention include, but are not limited to, hydrocarbons, including oils, such as aliphatic 6: hydrocarbon oils and naphthenic hydrocarbon oils, such as paraffin oils, mineral oils, vegetable oils, and kerosene, fatty esters, fatty acids, triglycerides, diglycerides, monoglycerides, alcohols, including polypropylene glycol and propoxylated or ethoxylated alcohols, ethers, amides, polyamides, cyclic hydrocarbons, propoxylated or ethoxylated acids, propoxylated or ethoxlyated glycerides, silicon hydrocarbons, saturated or unsaturated synthetic oils, perfumes, hydrocarbon-containing fragrance raw materials, including those containing alcoholic, cyclic, aldehydic, ether, unstauration, sulfur, and keto functionalities, and essential oils, insecticides, and insect repellants. Useful insect repellants include any volatile insect repellant, such as pyrethroid insecticides, Citronella, citronellol, nerol, geraniol, and N,N-Diethyl-m-toluamide (DEET). A preferred insect repellant is DEET.

One advantage of this invention is the ability of the microemulsion to incorporate water soluble additives and the compatibility of the water soluble additives in the resulting clear polymeric gel. Examples of water soluble additives that can be included in the microemulsion are pH color indicators, fluorescent dyes, water soluble dyes, and water soluble flavor and fragrance components. Specific examples include thymolphthalein and thymol blue pH color indicators.

Additionally, the present invention provides a method to produce the gel that comprises vigorously mixing (a) from 1–70 wt. %, preferably from 140 wt. %, and more preferably from 10–25 wt. % of an anhydride functionalized polymer, (b) from 0.1–40 wt. %, preferably from 0.1–20 wt. %, and most preferably from 0.5–5 wt. % of a cross-linking agent, (c) from 0.01–50 wt. %, preferably from 0.1–20 wt. %, and more preferably from 0.5–10 wt. % surfactant, (d) from 0.01–30 wt. %, preferably from 0.1–10 wt. %, and more preferably from 0.1–5 wt. % water, and (e) from 10.0–95.0 wt. % of a hydrophobic liquid, based on the total weight of the polymeric gel composition to form a microemulsion. In preferred embodiments, the combined proportion of (d) and (e) equals at least 30 wt. %, based on the total weight of the polymeric gel composition.

Vigorous mixing of the surfactant, water, and the hydrophobic liquid promotes the formation of the microemulsion Without wishing to be bound by a theory of the invention, it is believed that the microemulsion is characterized by the formation of water-in-oil micelles, that effectively minimize the diffraction of light in the visible wave-range.

The resulting microemulsion then reacts at ambient temperature and pressure to gel and form a clear, cross-linked polymer gel. In some embodiments, the microemulsion is placed in a mold where gelling occurs. The resulting structurally stable gel is then removed from the mold.

In some embodiments, the microemulsion is formed by first making two premixes, one containing the anhydride functionalized polymer and the other containing the cross-linking agent and then blending the premixes. For example, in one embodiment, the microemulsion is formed by combining a first premix containing the cross-linking agent and one or more of at least a portion of the hydrophobic liquid, the surfactant and the water with a second premix containing the cross-linking agent and one or more of at least a portion of the hydrophobic liquid, the surfactant and the water. In some embodiments the first premix contains the cross-linking agent, the surfactant, the water and all the hydrophobic liquid. In alternative embodiments, the second premix contains the anhydride functionalized composition and all the hydrophobic liquid.

EXAMPLES

The following examples are intended to further illustrate the invention and not to limit it.

Example 1

An aqueous gel was made using the following procedure. Premix A was made by combining 5.0 g of fragrance oil and 1.9 g of Lithene N4-9000-MA10 and mixed until homogeneous. Premix B was made by combining 2.4 g fragrance oil, 0.1 g water, 0.2 g Surfonic N40 and 0.3 g Jeffamine XTJ-403 and mixed until homogeneous. Premix A and Premix B were then combined and mixed vigorously for 15–30 seconds. This microemulsion was poured into a 2 inch diameter clear petri dish and the clarity was rated after the gel composition formed. The resulting gel was clear as seen in Table 1.

Example 2

An aqueous gel was made using the procedure described in Example 1, except that Premix B contained 2.5 g fragrance oil and Jeffamine XTJ-509. The resulting gel was clear as seen in Table 1.

Example 3

An aqueous gel was made using the procedure described in Example 1 except that Premix B contained 2.6 g fragrance oil and 0.2 g Surfonic L-24-3 and 0.2 g Jeffamine D-400. The resulting gel was clear as seen in Table 1.

Example 4

An aqueous gel was made using the procedure described in Example 1 except that Premix B contained 2.6 g fragrance oil and 0.2 g Surfonic 15-S-3 and 0.2 g Jeffamine D-400. The resulting gel was clear as seen in Table 1.

Example 5 (Comparative Example)

Aqueous gels were formed using the procedure described in Example 1 except as follows. Premix A contained 5.0 g fragrance oil and 1.9 g Lithene. Premix B contained 2.4 g fragrance oil, 0.1 g water, 0.3 g Jeffamine T-403 and one of the following surfactants, (a) 0.2 g Surfonic N85, (b) 0.2 g Surfonic N120, of (c) a mix of 0.1 g Surfonic N40 and 0.1 g Surfonic N85. None of these gels were clear as seen in Table 1.

Example 6 (Comparative Example)

An aqueous gel composition was formed using the procedure described in Example 1, except that premix B did not contain a surfactant. The resulting gel composition was not clear as seen in Table 1.

TABLE 1

| Experiment Number | Fragrance Oil | Lithens N4-9000-MA10 | Water | Surfonic N40 | Surfonic N85 | Surfonic N120 | Surfonic L-24-3 | Tergitol 15-S-3 | Jeffamine T-403 | Jeffamine XTJ-509 | Jeffamine D-400 | Result (1) |
|---|---|---|---|---|---|---|---|---|---|---|---|---|
| 1 | 7.4 | 1.9 | 0.1 | 0.2 | — | — | — | — | 0.3 | — | — | Clear |
| 2 | 7.5 | 1.9 | 0.1 | 0.2 | — | — | — | — | — | 0.3 | — | Clear |
| 3 | 7.6 | 1.9 | 0.1 | — | — | — | 0.2 | — | — | — | 0.2 | Clear |
| 4 | 7.6 | 1.9 | 0.1 | — | — | — | — | 0.2 | — | — | 0.2 | Clear |
| 5 | 7.4 | 1.9 | 0.1 | — | 0.2 | — | — | — | 0.3 | — | — | Hazy |
| 6 | 7.4 | 1.9 | 0.1 | — | — | — | — | — | 0.3 | — | — | Cloudy |

(1) The clarity of each gel composition was judged on a scale ranging from clear, hazy, cloudy, and opaque.

Example 7

An aqueous gel was made using the following procedure. Premix A was made by combining 10.0 g of fragrance oil and 3.8 g of Lithene N4-9000-MA10 and mixed until 11.1 homogeneous. Premix B was made by combining 5.0 g fragrance oil, 0.4 g water, 0.5 g. ethoxylated laural sodium sulfate, 0.1 g ethanol, 0.33 g Jeffamine D-400, and 0.1 g Jeffamine XTJ-509. Premix A and Premix B were then combined and mixed vigorously for 15–30 seconds. This microemulsion was poured into a 2 inch diameter clear petri dish and the clarity was rated after the gel composition formed. The resulting gel was clear as seen in Table 2.

Example 8

An aqueous gel was made using the procedure described in Example 7, except that Premix B contained 5.5 6 g fragrance oil, 0.15 g water, 0.3 g ethoxylated laural sodium sulfate, and 0.05 g ethanol. The resulting gel was clear as seen in Table 2.

Example 9

An aqueous gel was made using the procedure described in Example 7, except that Premix B contained 0.3 g water, 0.6 g ethoxylated laural sodium sulfate, and 0.1 g ethanol. The resulting gel was clear as seen in Table 2.

Example 10

An aqueous gel was made using the procedure described in Example 7, except that Premix B contained 4.6 g fragrance oil, 0.3 g water, 0.6 g. ethoxylated laural sodium sulfate, and 0.4 g Jeffamine T-403. The resulting gel was clear as seen in Table 2.

TABLE 2

| Experiment Number | Fragrance Oil | Lithene N4-9000 MA10 | Water | TEA Laural Sulfate | Laural Sulfate NH₃ salt | Alkyl Sulfonate Na salt | Ethoxylated Laural Na Sulfate | Ethanol | Jeffamine D-400 | Jeffamine XTJ-509 | Jeffamine T-403 | Result (1) |
|---|---|---|---|---|---|---|---|---|---|---|---|---|
| 7 | 15.0 | 3.8 | 0.4 | — | — | — | 0.5 | 0.1 | 0.33 | 0.1 | — | Clear |
| 8 | 15.5 | 3.8 | 0.15 | — | — | — | 0.3 | 0.05 | 0.33 | 0.1 | — | Clear |
| 9 | 15 | 3.8 | 0.3 | — | — | — | 0.6 | 0.1 | 0.33 | 0.1 | — | Clear |
| 10 | 14.6 | 3.8 | 0.3 | — | — | — | 0.6 | 0.1 | — | — | 0.4 | Clear |

(1) The clarity of each gel composition was judged on a scale ranging from clear, hazy, cloudy, and opaque.

Example 11

An aqueous gel was made using the following procedure. Premix A was made by combining 10.0 g of fragrance oil and 3.8 g of Lithene N4-9000-MA10 and mixed until homogeneous. Premix B was made by combining 4.8 g fragrance oil, 0.3 g water, 0.3 g ethoxylated laural sodium sulfate, 0.1 g ethanol, 0.4 g Jeffamine D-400, and ca. 0.001 g LX1926 Pylachrome Purple. Premix A and Premix B were then combined and mixed vigorously for 15–30 seconds. This microemulsion was poured into a 2 inch diameter clear petri dish and the clarity was rated after the gel composition formed. The resulting gel composition was clear and the purple color was uniformly distributed throughout the gel.

Example 12

An aqueous gel was made using the following procedure. Premix A was made by combining 5.0 g DEET and 1.9 g of Lithene N4-9000-MA10 and mixed until homogeneous. Premix B was made by combining 2.2 g fragrance oil, 0.15 g water, 0.05 g ethanol, 0.4 g Jeffamine T-3000. Premix A and Premix B were then combined and mixed vigorously for 15–30 seconds. This microemulsion was poured into a 2 inch diameter clear petri dish and the clarity was rated after the gel composition formed. The resulting gel composition was clear.

Example 13

An aqueous gel was made using the procedure described in Example 12 except that Premix B contained 2.2 g of fragrance oil instead of DEET. The resulting gel was clear.

Example 14 (Comparative Example)

An aqueous gel composition was formed as described in U.S. Pat. No. 4,362,841. Microemulsion A was formed by combining 10 g fragrance oil, 10 g maleinized polyisoprene (LIR-403), 11.0 g Epicote 828, 0.5 g Ancamine K-54 and 1.5 g Surfonic L-24-3. Into this microemulsion 0.1, 0.4 or 5.0 g of water was slowly added while mixing. None of the resulting gels were clear.

Example 15 (Comparative Example)

An aqueous gel composition was formed as described in U.S. Pat. No. 5,334,691. The following materials were combined as described in the patent: 74.8 g Carbowax 8000, 2.1 g Diethylene Glycol, 22.1 g Desmodur W, 1.0 g water, 0.2 g catalyst and 13.6 g urea. The resulting gel composition was not clear.

The inventive gel compositions are compatible with both hydrophobic liquids and water soluble materials and are aesthetically pleasing and functionally appropriate. It should be understood that the examples and embodiments described herein are for illustrative purposes only and that various modifications or changes in light thereof will be suggested to persons skilled the art and are to be included within the spirit and purview of this application and the scope of the appended claims.

What is claimed is:

1. A crosslinked, polymeric gel composition comprising the reaction product of a microemulsion containing:
   (a) from 1–70 wt. % of an anhydride functionalized polymer;
   (b) from 0:140 wt. % of a cross-linking agent;
   (c) from 0.01–50% wt. % surfactant;
   (d) from 0.01–30 wt. % water and
   (e) from 10–95 wt. % of a hydrophobic liquid, based on the total weight of the polymeric gel composition;
   wherein said composition is substantially clear.

2. The polymeric gel composition of claim 1 wherein the anhydride functionalized polymer is present in an amount from 1–40 wt. %, the cross-linking agent is present in an amount from 0.1–20 wt. %, the surfactant is present in an amount from 0.1–20 wt. %, and the water is present in an amount from 0.1–10 wt. %.

3. The polymeric gel composition of claim 1 wherein the anhydride functionalized polymer is present in an amount from 10–25 wt. %, the cross-linking agent is present in an amount from 0.5–5 wt %, the surfactant is present in an amount from 0.5–10 wt. %, and the water is present in an amount from 0.1–5 wt %.

4. The polymeric gel composition of claim 1 wherein the combined proportion of (d) and (c) equals at least 30 wt. %, based on the total weight of the polymeric gel composition.

5. The polymeric gel composition of claim 1 wherein the anhydride functionalized polymer is a maleinized polybutadiene polymer, a maleinized polyisoprene polymer, a maleinized polybutadiene/styrene polymer or a mixture thereof.

6. The polymeric gel composition of claim 1 wherein the cross-linking agent is water soluble.

7. The polymeric gel composition of claim 1 wherein the cross-linking agent is a polyamine compound.

8. The polymeric gel composition of claim 1 wherein the surfactant is an anionic or a nonionic surfactant.

9. The polymeric gel composition of claim 1 wherein the microemulsion further comprises a water soluble colorant, a water soluble dye, a water soluble pH color indicator or a water soluble pigment.

10. The polymeric gel composition of claim 1 wherein the microemulsion further comprises a water soluble fragrance or flavor material.

11. A clear, crosslinked, polymeric gel composition comprising the reaction product of a microemulsion containing:

(a) from 1–40 wt. % of an anhydride functionalized polymer selected from maleinized polybutadiene polymers, maleinized polyisoprene polymers, maleinized polybutadiene/styrene polymers or mixtures thereof;
(b) from 0.1–20 wt. % of a polyamine cross-linking agent;
(c) from 0.1–20% wt % anionic or cationic surfactant;
(d) from 0.1–10 wt. % water, and
(e) from 10—95 wt. % of a hydrophobic liquid perfume, a hydrophobic liquid insecticide or a hydrophobic liquid insect repellant, based on the total weight of the polymeric gel composition, with the combined proportion of (d) and (e) equaling at least 30 wt. %, based on the total weight of the polymeric gel composition.

12. The method of claim 11 wherein the anhydride functionalized polymer is present in an amount from 10–25 wt. %, the cross-linking agent is present in an amount from 0.5–5 wt. %, the surfactant is present in an amount from 0.5–10 wt. %, and the water is present in an amount from 0.1–5 wt. %.

* * * * *

UNITED STATES PATENT AND TRADEMARK OFFICE
CERTIFICATE OF CORRECTION

PATENT NO. : 6,846,491 B1
DATED : January 25, 2005
INVENTOR(S) : Randall Richards It is certified that error appears in the above-identified patent and that said Letters Patent is hereby corrected as shown below:

<u>Title page,</u>
Item [73], Assignee, should read -- International Fragrance & Technology --

Signed and Sealed this

Tenth Day of May, 2005

JON W. DUDAS
*Director of the United States Patent and Trademark Office*